United States Patent [19]

Striepeke et al.

[11] Patent Number: 5,672,881
[45] Date of Patent: Sep. 30, 1997

[54] CHARGE-COUPLED DEVICE IMAGING APPARATUS

[75] Inventors: Steven K. Striepeke, Sebastopol; Peter Edridge, Fairfax; Christopher M. Starr, Sonoma; John C. Klock, Nicasio, all of Calif.

[73] Assignee: Glyko, Inc., Novato, Calif.

[21] Appl. No.: 612,195

[22] Filed: Mar. 6, 1996

Related U.S. Application Data

[63] Continuation of Ser. No. 306,068, Sep. 14, 1994, abandoned.
[51] Int. Cl.$^6$ ............................................. G01N 21/64
[52] U.S. Cl. ............................. 250/461.2; 250/458.1
[58] Field of Search ......................... 250/461.2, 458.1, 250/459.1, 461.1, 251.1 A

[56] References Cited

U.S. PATENT DOCUMENTS

| | | | |
|---|---|---|---|
| 4,479,062 | 10/1984 | Kawasaki et al. | 348/298 |
| 4,874,492 | 10/1989 | Mackay | 204/182.8 |
| 5,205,917 | 4/1993 | Klock, Jr. | 204/182.8 |
| 5,304,809 | 4/1994 | Wickersheim | 250/458.1 |
| 5,308,460 | 5/1994 | Mazid et al. | 204/180.1 |
| 5,340,453 | 8/1994 | Jackson | 204/299 R |

OTHER PUBLICATIONS

Advertisement entitled, "With Glyco FACE technology you can separate, quantify, or sequence your carbohydrate . . . In one day.," Jul. 15, 1993, *Nature* 364, No. 6434:8–9.

Advertisement entitled, "With Glyco FACE technology you can separate, quantify, or sequence your carbohydrate . . . In one day.," Aug. 5, 1993, *Nature* 364, No. 6437:8–9.

Brochure entitled, "Glyco SE1000, FACE™ Workstation".

Shauna S. Roberts, Nov. 1992, "Scanners And More: Acquiring Electrophoresis Images for Computer Analysis," *The Journal of NIH Research* 4:81–90.

*Primary Examiner*—Carolyn E. Fields
*Attorney, Agent, or Firm*—Pennie & Edmonds LLP

[57] ABSTRACT

An apparatus for fluorescence of a biological sample includes a light illumination source, an ambient light-excluding optical chamber, a sample holder, a two-dimensional array charge coupled device ("CCD") sensor providing for on-chip signal integration of each pixel of the array, and an analog/digital converter for digitizing the CCD signal. Signal acquisition time from the array is varied so that the integrated signal from each pixel is below its saturation level. A darkfield value for each pixel is acquired and subtracted from the illuminated signal from that pixel so as to yield a darkfield corrected signal. The fluorescence value for each pixel can be compensated for variations in excitation energy reaching different sample areas. Image readout is through a single channel output.

8 Claims, 1 Drawing Sheet

CHARGE-COUPLED DEVICE IMAGING APPARATUS

This is a continuation of application Ser. No. 08/306,068, filed Sep. 14, 1994, now abandoned.

1. Field of the Invention

The subject invention is in the field of electronic imaging. In particular, the invention pertains to apparatus and methods for light imaging of fluorescent or non-fluorescent materials, and electronic storage and analysis of the imaging data so acquired.

2. Background of the Invention

The need to obtain a permanent image or picture of a light-emitting object or display arises frequently in scientific, engineering, and biomedical disciplines. The most common means for recording a light image is by means of a photographic film camera. Photographic recording of scientific and technical experiments offers the advantages of using relatively simple, ubiquitous apparatus and familiar procedures. However, photographic procedures suffer significant disadvantages, notably: (1) the time lag imposed by the necessity for film development; (2) the frequently non-quantitative or semiquantitative nature of the stored image; and (3) storage of the image as analog rather than digital data. These disadvantages hinder the use of photographic data storage and archiving in computer-based image analyses.

The use of computer-based image analysis techniques in biological and biochemical investigations has increased with the need to provide precise image analysis and quantitation. The technique of gel electrophoresis, which is routinely employed to quantitatively analyze biomolecules, requires calculation of the relative migration distance of a sample compound versus reference compounds in order to determine the molecular size of the sample compound. The intensity of the band representing the sample compound after suitable staining provides a means of quantitating the compound. Both the migration distance measurement and the intensity measurement should be performed and recorded for use in image analysis techniques.

Currently most of the imaging in biology or biochemistry is done either with photographic film cameras or with video cameras having silicon chips or charged-coupled devices ("CCD") as the light sensing material. A comprehensive review of the currently available image-analysis systems for electrophoresis and blotting may be found in Roberts, "Scanners and More: Acquiring Electrophoresis Images for Computer Analysis", *The Journal of NIH Research*, November 1992, Vol. 4, pages 81–91.

When the electrophoresis gel is recorded using a photographic film camera, data analysis is often accomplished by hand measurement of the migration distance and semiquantitative estimation of band intensity. Alternatively, either the photograph or the gel itself may be scanned by a densitometer to generate a quantitative readout. When the gel is recorded using a video camera, the data necessarily are obtained in an electronic form, which under appropriate conditions could be adapted for computerized image processing.

A general image-processing system consists of several components: (1) the sensor, (2) the analog-to-digital ("A/D") converter, (3) the digital processor, and (4) the display. The sensor converts spatially-distributed light intensities into analog electrical signals, and the A/D converter transforms the signal into the digital form required for processing. The digital processor comprises general purpose or dedicated computer elements including arithmetic functions, active and storage memory, and input/output drivers coupled with a software program.

Most currently available photodocumentation systems consist of these four elements, each of which is provided as a separate component. Usually each such component is available commercially as a stand-alone apparatus. Consequently, in order to construct a complete image analysis system, the user often needs to assemble separate pieces of equipment and connect them with electronic cables. As a result these systems often are large, cumbersome, and expensive devices which are inconvenient to use.

Moreover, the use of a scanning device as a sensor imposes several limitations. Most scanning devices use linear array CCD detectors, rather than rectangular array devices. Linear array CCDs accumulate one line of data at a time, and must scan a two-dimensional sample line by line. This scanning requirement lowers the sensitivity of the measurement and increases the time needed to read the entire sample. With samples which are unstable due to effects such as photobleaching or band diffusion from unfixed electrophoretic gels, these limitations of linear array detectors are significant.

Conventional video cameras are not suitable for use as the scanning device. Although video cameras use two-dimensional CCD area arrays, they are limited in that the time of signal acquisition is fixed. If certain pixels of the CCD are exposed to high light signal levels, they may become saturated during the fixed acquisition time, and therefore yield nonlinear values. Similarly, pixels which are exposed to low light signal levels may accumulate, during a fixed acquisition time, integrated signal values which are barely above the dark current and therefore difficult to distinguish or measure accurately.

A further limitation of video cameras is that their output is an analog signal containing screen blanking and synchronization pulses necessary for display on television monitors. This output is unsuitable for digital signal processing.

SUMMARY OF THE INVENTION

The present invention resolves these problems in a novel imaging apparatus which provides rapid image acquisition, relative to conventional scanning devices. Rapid image acquisition of chemical samples is critical due to rapid analyte degradation through photo-bleaching and diffusion.

The present invention also provides for precise, reproducible positioning of the gel cassette within the optical path. Reproducible positioning is necessary to permit reproducible metrology with repeated imaging of a single gel or between multiple gels.

A preferred aspect of the present invention relates to the employment of a charged-coupled device imaging sensor for on-chip integration that does not require cooling. A cooled CCD may be used to increase sensitivity although the ability to run a charged-coupled device under ambient conditions provides enormous benefits in terms of simplicity of apparatus. It does require, however, the application of corrections for sensor defects and for thermal and electronic noise.

The present invention provides for the reception and processing of output from the imaging device in a manner that preserves a one-to-one correspondence, both quantitatively and geographically, between the image detection device and the display device. That is, the present invention provides an apparatus which may be used to sample and digitize charge from each imaging device pixel prior to, rather than subsequent to, any storage or processing operations.

Specifically, the present imaging, measurement, and archiving apparatus for light imaging of a biological sample includes means for illuminating a sample to selectively excite molecules therein and cause fluorescence, a two-dimensional charged-coupled device detector array positioned to detect fluorescent emissions from the sample, means for varying the signal acquisition time from the charged-coupled device detector array so that the integrated signal from each pixel of the charged-coupled device detector array is below its saturation level, means for acquiring a darkfield value for each pixel of the charged-coupled device detector array and subtracting the darkfield value from the illuminated signal from that pixel to yield a darkfield-corrected signal, and means for reading out the darkfield-corrected signal to a visual display unit thereby producing a two-dimensional gray scale image of the sample.

In the light imaging apparatus of the present invention, the means for illuminating the sample, the means for varying the signal acquisition time, and the means for acquiring a darkfield value may all be provided within an enclosure that excludes ambient light. That light-excluding enclosure will normally contain the illumination source, a sample holder, and a charged-coupled device detector array positioned to detect fluorescent emissions from the sample.

The light imaging apparatus of the present invention may further include means for operating the charged-coupled device detector array at ambient temperature in an on-chip integrating mode under the control of a computer programmed to have the capability of varying signal acquisition time from the CCD detector array, converting the signal from each pixel of the detector array to a digital value, and storing the digital values as an array of values in memory accessed by the computer. The computer may also be programmed to be able to acquire a brightfield correction value for each pixel in the absence of the sample, and the darkfield-corrected value of the illuminated signal from each pixel may be multiplied by its brightfield correction value prior to readout to the display.

In its most preferred aspects, the present invention additionally provides three enhancements that make the system even more accurate and flexible. Accuracy is increased by flat-field correction and single-channel readout features. All of these features are discussed in detail hereinbelow. The invention also provides methods of imaging, measuring, and archiving samples using the apparatus described herein.

DETAILED DESCRIPTION OF THE INVENTION

Figure 1:
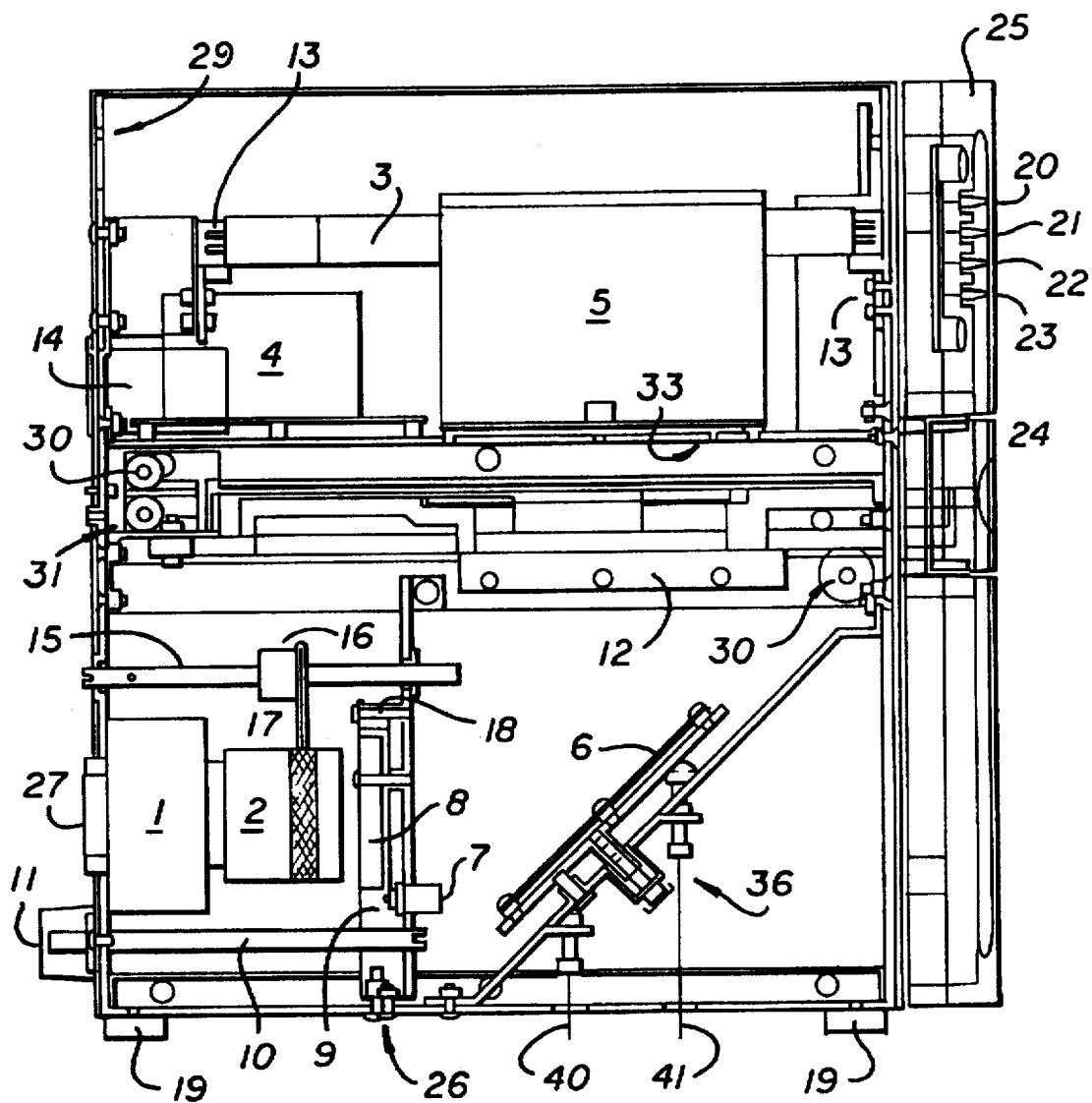
FIG. 1 is a cutaway side view of an embodiment of an apparatus of the present invention.

A preferred embodiment of the apparatus of the present invention comprises a light illumination source, an ambient light-excluding optical chamber, a sample holder, a two-dimensional array CCD sensor providing for on-chip signal integration of each pixel of the array, and an analog/digital converter for digitizing the CCD signal. In this preferred embodiment, exposure time of the CCD imaging chip is controlled by a computer's central processing unit ("CPU") controller via a programmed autoexposure feature or via an operator-specified instruction. The fluorescent light emitted from the material to be imaged is detected by the solid-state light-detecting chip in the CCD camera, and integrated over the exposure time. The resulting analog signal is read out into an A/D converter and converted to digital form. The spatially-encoded digital signal is transmitted to a computer CPU and stored, usually in random-access memory ("RAM").

Software may then be used to process the data and reconstruct the image by methods that are in general known to those skilled in the art. Preferred data processing may include subtraction from the raw signal value for each pixel of its respective dark current, and multiplying the darkfield-corrected value for each pixel by a brightfield correction factor to yield a brightfield-corrected value for each pixel. The resulting electronic image data can then be displayed on a monitor and/or archived by the computer for retrieval at a desired time.

In certain preferred embodiments, a darkfield correction value is acquired under computer control for each pixel of the CCD array in the absence of illumination and therefore absence of signal. This darkfield correction value represents dark current (or "noise"), and the corresponding value is subtracted from the value of the signal in each pixel to yield a darkfield-corrected signal.

In other preferred embodiments, a brightfield correction factor may be obtained for each pixel of the CCD in the absence of sample, by replacing the sample with a uniformly emitting substrate such as a fluorescent film of MYLAR or the like, and accumulating the signal under illumination of the substrate. The variation in intensity of illumination at various positions on the emitting substrate is caused by non-uniformity of the light source, and results in corresponding position-dependent variation of the signal intensity among the pixels of the CCD. Variation of signal intensity among pixels also occurs because of their variation in light sensitivity. The reciprocal of the dark current corrected brightfield intensities gives a brightfield correction factor for each pixel. To use these brightfield correction factors, the darkfield-corrected value of the signal for each pixel obtained in the presence of a sample is then multiplied by its brightfield correction factor prior to its storage in memory as a brightfield-corrected value in an array for that sample. The array of brightfield-corrected values may be read out to a display screen.

The sample or object to be imaged may be placed into a sliding drawer cassette sample holder for reproducible positioning of the sample or object. A particularly preferred sample holder accommodates an electrophoresis gel, especially a gel suitable for carbohydrate electrophoresis as described in U.S. Pat. No. 4,874,492 and application No. 07/938,832, the contents of which are expressly incorporated herein by reference thereto.

The apparatus may optionally further comprise any of several additional features such as: an adjustable mirror assembly for directing light from the sample onto the CCD sensor array; an excitation filter holder with one or a plurality of interchangeable filters; an emission filter holder with one or a plurality of interchangeable filters; a sliding tray assembly for reproducibly positioning the sample; a light source and collimating reflector assembly; an electronic input-output interface such as an ISA bus for communicating with the CPU controller and data storage device; and a CCD digital camera sensor comprising lens, housing, CCD silicon chip, and onboard electronic amplifier and A/D components to receive the signal from the CCD and convert the analog electrical current to a digital signal. Other optional parts may include ports and assemblies for focusing the lens, adjusting the mirror and filters, and indicator light-emitting diodes to determine the mechanical and electrical status of the apparatus.

Illumination of the sample

The light illumination source may be of any type emitting radiation within the appropriate wavelength range. Exemplary sources include incandescent light bulbs, halogen lamps, mercury vapor lamps, light-emitting diodes, fluorescent lamps, lasers, or infrared sources. In most cases a single source is sufficient, but a plurality of sources, including an array of sources, is also possible. The light source or sources may be aided by reflectors or mirrors to direct radiation onto the sample.

For many applications, the light source preferably will be arranged to provide illumination of the sample which is as uniform as possible. Multiple sources of light are difficult to focus uniformly on the sample. Also, multielement light sources are difficult to keep balanced, since tube or bulb output will often diminish unequally with age. A preferred light source, therefore, comprises a single element with a collimating reflector. However, as described hereinbelow, a most preferred embodiment provides electronic means for correcting for the nonuniformity of illumination. Therefore, substantial nonuniformity of illumination is tolerable.

The wavelength range of illumination may be selected depending upon the absorption, excitation, or light-scattering properties of the sample. When a chromophore or fluorophore is used for detection, the light source should emit radiation within the absorption or excitation bands of the chromophore or fluorophore. Further details on the use of fluorophores for detection may be found in U.S. Pat. Nos. 5,308,460; 5,205,917; and 4,874,492, the disclosures of which are hereby expressly incorporated by reference.

FLAT FIELD CORRECTION. The ultraviolet light source that excites fluorophores in the gel does not provide perfectly uniform illumination over the entire area of the gel. Due to the multiple paths for the illuminating light to reach the center of the gel area and fewer paths that lead to the edges, excitation light energy is less at the edges than at the center. This discontinuity of illumination is a stable feature of the physical design of the apparatus. Therefore, variations in the light intensity pattern may be recorded, for instance in a computer file. The intensity variations may be recorded by acquiring a noncorrected image of a uniformly fluorogenic sheet in the place of a gel cassette. The fluorescent output of the sheet is proportional to the incident excitation energy. The stored image file becomes a pixel-by-pixel reference for the necessary correction. In the case of the brightest pixels, generally those at the center of the gel, the correction factor would be about the same as the fluorescence value recorded from a specimen gel. Near the edge of the gel where the incident excitation energy is about 75% of that at the center, the correction factor derived from the flat field correction file would be 1.333 times the fluorescence value. In this way, features of equal fluorogenic potential may be recorded with equal intensity in the corrected image file.

With many light sources, the emitted radiation includes wavelengths outside the region of absorption or excitation; this extraneous irradiation does not enhance the signal, and may interfere with accurate measurement. Consequently, a filter between the light source and sample is often desirable. Filters may be any of several types, such as colored glass or gelatin filters. However, in many cases an interference filter is advantageous because its wavelength of maximum transmittance and bandwidth can be tailored to the wavelength characteristics of the chromophore or fluorophore.

The invention provides a sample holder and positioner. In the case of substantially two-dimensional samples (i.e., one having a thickness that is less than 10% of the length or width dimensions), the sample holder may be a sliding tray or drawer, which fits into a slot having stops, retractable spring-loaded pins, or similar means for reproducibly positioning the sample in the zone of illumination. The slot or the sliding tray may be fitted with elastic or flexible skirts or gasket material to seal the opening against extraneous light when the sample is in place.

Light emitted from the illuminated sample, whether as fluorescence emission, transmitted light, or scattered light, is directed onto the CCD detector array. In some cases the sample-emitted light may be directed through an emission-side filter, a lens, or a mirror prior to impinging upon the CCD detector. It is preferred to detect fluorescent emissions from the sample. An emission-side filter is preferred for removing transmitted exciting light when fluorescent signals are to be detected. The filter is chosen to exclude excitation wavelengths, and transmit maximally in the emission wavelengths of the fluorophore. Optionally, multiple filters may be provided to optimize different measurements. A sliding filter holder may be used to facilitate repositioning of filters. A lens or mirror may be used to direct or focus the emitted light onto the CCD detector array surface.

The charged-coupled device

The CCD detector preferably is a two-dimensional ("2-D") rectangular or square area array of pixels. A full-frame acquisition 2-D array is preferred, because it permits rapid acquisition of multiple images. The CCD detector array may be either cooled or non-cooled. Although cooling lowers the random thermal noise in the detector, cooling imposes the disadvantages of greater cost, inconvenience, loss of sensitivity due to an additional optical window, and condensation on cooled surfaces. In a preferred embodiment of the invention, the CCD detector is operated at ambient temperature. Signal averaging and dark current subtraction may be used to compensate for the increased noise from ambient temperature operation.

In a preferred embodiment, the CCD detector array is used as a digital camera rather than as a video camera. A significant difference between these camera types is that a digital camera acquires the image, i.e., the signal in each pixel, and digitizes the output of each pixel via an A/D converter for transmission to the CPU of the computer controlling the data acquisition. By contrast, a video camera produces an analog output, with screen blanking and synchronization pulses for display on TV-type monitors. The output of a video camera is not suitable for digital signal processing because the one-to-one correspondence between the pixel datum in the CPU memory and the corresponding pixel in the detector array would be lost. Thus, corrections for sensor array defects, which are dependent upon that relationship, cannot be made on a video camera.

The digital camera provides on-chip integration of the signal over a variable signal acquisition time. By contrast, video cameras which purport to provide signal integration typically are used with a so-called frame storage box, which contains a memory in which a predetermined number of frames are added to build up an image. The video camera typically has a fixed integration time dictated by conventional television broadcasting standards, providing an integration time of about $1/60$ to $1/30$ of a second.

Unlike these video camera integration devices, the digital CCD camera in a preferred embodiment of the invention permits variable signal acquisition and integration time, either under the control of the CPU and its software or under a user override command. The CPU controls the duration of the interval during which signal is added into each pixel.

This signal addition process inherently integrates the signal over the acquisition time. Using the provided software, the CPU can vary the signal acquisition time in order to keep the signal in the most intense pixel below the saturation level. In this way, the computer-controlled variation of acquisition time insures that the entire CCD array is operating in the region of linear response and therefore providing accurate quantitation.

In implementing this acquisition time control, signal is initially acquired for a brief initial acquisition time and the output of each pixel is scanned to determine that all pixels are below saturation. If any are saturated, the acquisition time is iteratively shortened until subsaturation is achieved. At this point, acquisition time may be scaled up by an appropriate linear factor to put the most intense pixel at a value close to saturation, e.g., 90%. This adjustment of acquisition time requires only about 5 seconds before a measurement.

Dark current preferably also is measured for each pixel in the absence of illumination and therefore of signal. The darkfield correction value is subtracted from the measured value in the presence of signal, i.e., under sample illumination.

Preferably, a brightfield correction value is also obtained by illuminating a uniformly emitting substrate positioned in the sample holder, such as a sheet of fluorescent plastic. MYLAR is a typical material that can be used for this purpose. This procedure corrects for nonuniformity of illumination. The measured value with an actual sample is divided by the brightfield correction value to normalize the measurements.

A preferred CCD digital camera also contains an output signal amplifier to minimize the effect of ingress of external electromagnetic noise on the signal transmission line to the computer interface board. The camera assembly may be contained in a second light-excluding enclosure incorporating a lens for collecting light from the sample and focusing it onto the CCD imaging device.

The CCD camera is electronically connected through a CPU interface which allows for camera control circuitry and an analog-to-digital converter. The CPU may be an onboard chip or may be the CPU of an external computer such as a PC, and is interfaced with the CCD and A/D converter through a suitable electronic input-output means, such as an ISA bus. The CPU directs the readout of the signal from each pixel of the camera's CCD. The signal from each pixel is independently routed to the A/D converter, where the signal is digitized. Each signal then is stored in the CPU's RAM for subsequent processing.

FIG. 1 depicts a cutaway side view of a particular embodiment of a novel device arranged to practice the method of the present invention. In FIG. 1, 1 is a light-tight enclosure that contains a CCD camera. A preferred model of CCD camera is made by Electrim Coproration, Model EDC-1000HR. Characteristics of this camera include a monochrome, frame-transfer area array CCD detector (Texas Instruments CCD chip TC-241 or equivalent), digitally controlled, digital output, control and output via an ISA bus adaptor for a personal computer.

The enclosure 1 also contains an output signal amplifier to minimize the effect of the ingress of external electromagnetic noise on the signal transmission line to the computer interface board. Camera enclosure 1 is constructed so as to provide a precise location of lens relative to the CCD camera. 27 is an electrical connection for the camera interface cable.

2 is a lens for collecting light from the object being imaged. Lens 2 focusses light from the object on the CCD camera. The operator may adjust the focus point of lens 2 by activating focus adjustment control shaft 15 which is provided with a slot to receive a focus adjustment tool. Focus adjustment control shaft 15 can revolve drive pulley 16 which in turn will move focus adjustment drive belt 17 to adjust the focus of lens 2.

3 is a light source, which may be incandescent, arc, fluorescent, or a combination of these. 13 is a light source holder and electrical connector. 5 is a collimating reflector to direct light uniformly toward the sample area.

Excitation filter 33 blocks light within the bandpass of the emission filter from the camera compartment. Position and surface coating of the excitation filter are important. The filter should be positioned such that debris from the sample will not be able to fall onto the filter. Dust, gel fragments, or droplets of liquid on the excitation filter may obscure the image of the gel. The excitation filter should, therefore, not be positioned so that gravity or air currents Will cause debris to contaminate the filter's surface. The excitation filter will preferably be coated with a hard coating that does not reflect light toward the detector that is within the bandpass of the emission filter. Otherwise, double images of the banding pattern of the gel may be observed.

6 is a mirror for folding the optic path. This permits a reduction in the overall dimensions of the instrument. 36 is an adjustable mirror assembly, which is controlled by axis adjustment controls 40 and 41, where 40 is an x-axis adjustment mechanism and 41 is a y-axis adjustment mechanism.

Electrical power is provided by direct current power supply 4, which also includes an indicator control circuit board. 14 is an alternating line current input with a main power on-off switch, fuses, and a spare fuse holder. 20 is a power on/off indicator lamp. 21 and 22 are filter in-use indicators. 23 is a camera in-use indicator.

Sample holder tray 24 moves along sample holder tray guide 12 over sample tray rollers 30 until it engages spring-loaded sample tray catch 31. Front panel 25 blocks the ingress of light around sample holder tray 24.

Front panel 25 additionally provides cosmetic edifice. Other aspects of the cosmetic edifice are provided by chassis and external rear and bottom panels 29. Feet 19 serve to raise the instrument above the surface that it is set upon, thus permitting the circulation of air underneath the instrument. Each foot 19 is made of material that has a high coefficient of friction in order to prevent lateral movement of the instrument while sample holder tray 24 is operated.

Emission filter 8 rejects excitation light emitted by the sample and passes light emitted from fluorophore in the direction of the CCD camera. Spring-loaded plunger 7 retains emission filter holder 9 in position. 9 is a movable holder that accommodates multiple emission filters. The operator is enabled to change emission filters without disassembling the instrument by turning filter changer control knob 11, which turns emission filter holder rotation shaft 10. Lock-down screw 26 prevents movement of emission filter holder 9. The current position of movable emission filter holder 9 is monitored by filter holder position detector switch 18.

Software operations

In utilizing the apparatus of the present invention, computer programming may advantageously be utilized to carry out the following steps:

1. Obtain a short, unprocessed image in order to allow the operator to define the area of interest.

2. Obtain a short, unprocessed image in order to determine the maximum integration time for the most brightly illuminated pixel in the operator-defined area of interest. This provides exposure control, causing the most brightly illuminated pixels to acquire the maximum number of photons without saturation. The operator may set an override parameter to allow a defined area percentage of the gel image to integrate beyond exposure if desired. In this way, very bright features can be presented side-by-side with the faintest features. When this override option is employed, of course, quantitative data for the bright features will not be obtainable.

3. Gather a quantity of frames, typically 4 or 8, at the integration time determined in step 2. As each frame is read out, add the new data to data in a matrix composed of 16-bit cells for each pixel. In this way, random noise will provide a sum with nearly uniform values. True signal from the fluorescent emissions will add to a sum greater than dark current noise.

4. Prompt the operator to remove the gel.

5. Gather a quantity of frames, typically 4 or 8, without the fluorescent gel in the optic path. As each frame is acquired, add the data to a 16-bit matrix in memory. This step serves multiple functions. First, dark current noise is determined for subtraction from the illuminated image. Second, pixel nonuniformity is mapped. Nonuniformity of pixel response, characterized by cold and hot pixels, can be dealt with by finding pixels with values that lie outside of the mean value for pixels in their region on the detector. Use the pixel values surrounding the nonuniform pixel to interpolate the correct value of the bad pixel. Without this adjustment, light and dark pixels would pepper the image.

A copy of software which can be used to carry out this invention is annexed hereto as Appendix A.

SINGLE-CHANNEL READOUT. Typical area-array CCD imaging chips have been developed for video camera applications in which chip readout time is of greater importance than is image clarity. Multiple output channels from the chip are used to increase the readout speed of these CCD chips. The multichannel output is subject to intensity variations from one channel to the next which are caused by thermal and various electrical effects on the electronics that handle the signals from the separated channels. One approach to dealing with this problem is to correct the values for the data coming from the highest and lowest output channels using the median values of the remaining channel as a reference. This smoothing correction, however, does produce some loss of real data. An enhanced approach that is preferred in accordance with the present invention, therefore, is to obtain the image readout from the CCD imaging chip through a single channel output.

Although this invention has been described with reference to various currently preferred and specific embodiments thereof, various other and different embodiments of the present invention will readily occur to those skilled in the art based upon the principles set forth herein. The present invention is to be limited, therefore, solely by the spirit of the disclosure hereinabove and by the scope of the appended claims.

What is claimed is:

1. An apparatus for imaging of a biological sample comprising means for illuminating the sample to selectively excite molecules therein and cause fluorescence, a two-dimensional cooled or non-cooled charge-coupled device detector array positioned to detect fluorescent emissions from the sample, means for varying the signal acquisition time from said charge-coupled device detector array so that the integrated signal from each pixel of said charge-coupled device detector array is below its saturation level, means for acquiring a darkfield value for each pixel of said charge-coupled device detector array and subtracting said darkfield value from the illuminated signal from that pixel to yield a darkfield-corrected signal, means for reading out said darkfield-corrected signal to a visual display unit thereby producing a two-dimensional gray scale image of the sample, and means for operating said charge-coupled device detector array at, or below, ambient temperature in an on-chip integrating mode under the control of a computer programmed to have the capability of varying signal acquisition time from said charge-coupled device detector array, converting the signal from each pixel of the charge-coupled detector array to a digital value, and storing said digital values as an array of values in memory accessed by said computer, and wherein the computer is programmed to be able to acquire a brightfield correction value for each pixel in the absence of the sample, and to multiply the darkfield-corrected value of the illuminated signal from each pixel by its brightfield correction value prior to readout to the display unit.

2. The light imaging apparatus of claim 1 in which said illuminating means, said means for varying the signal acquisition time, and said means for acquiring a darkfield value are all provided within an enclosure that excludes ambient light, said enclosure also containing a sample holder, and said charge-coupled device detector array.

3. The light imaging apparatus of claim 1 wherein the imaged portion of the sample has a diameter of at least 1 centimeter.

4. The light imaging apparatus of claim 1 further comprising a sample holder wherein the sample holder comprises means for reproducible positioning of an electrophoresis gel cassette.

5. The light imaging apparatus of claim 1 wherein the illuminating means includes a single-element ultraviolet illuminating means so that the sample is illuminated with ultraviolet light that is uniformly focussed on the sample.

6. The light imaging apparatus of claim 1 further comprising a filter positioned between the illuminating means and the sample.

7. An apparatus for light imaging of a translucent sample comprising means for illuminating the sample to selectively excite molecules therein and cause fluorescence, a two-dimensional charge-coupled device detector array positioned to detect fluorescent emissions from the sample, means for varying the signal acquisition time from said charge-coupled device device detector array so that the integrated signal from each pixel of said charge-coupled device detector array is below its saturation level, means for acquiring a darkfield value for each pixel of said charge-coupled device detector array and subtracting said darkfield value from the illuminated signal from that pixel to yield a darkfield-corrected signal, means for reading out said darkfield-corrected signal to a visual display unit thereby producing a two-dimensional gray scale image of the sample, and means for correcting the fluorescence value recorded for each pixel to compensate for the variation in incident energy to which that pixel is subjected due to variations in excitation energy reaching different areas of the sample contained in the imaging apparatus.

8. An apparatus for light imaging of a translucent sample comprising means for illuminating the sample to selectively excite molecules therein and cause fluorescence, a two-dimensional charge-coupled device detector array positioned to detect fluorescent emissions from the sample, means for varying the signal acquisition time from said charge-coupled device detector array so that the integrated signal from each pixel of said charge-coupled device detector array is below its saturation level, means for acquiring a darkfield value for each pixel of said charge-coupled device detector array and subtracting said darkfield value from the illuminated signal from that pixel to yield a darkfield-corrected signal, means for reading out said darkfield-corrected signal to a visual display unit thereby producing a two-dimensional gray scale image of the sample, and means for obtaining the image readout from the charge-coupled device detector array through a single channel output.

* * * * *